United States Patent [19]

Kalina

[11] Patent Number: 4,992,370
[45] Date of Patent: Feb. 12, 1991

[54] PROCESS FOR THE PRODUCTION OF ALCOHOL

[75] Inventor: Vladimir Kalina, Laussane, Switzerland

[73] Assignee: Nestec S.A., Vevey, Switzerland

[21] Appl. No.: 384,860

[22] Filed: Jul. 21, 1989

Related U.S. Application Data

[63] Continuation of Ser. No. 774,184, Sep. 9, 1985, abandoned, which is a continuation of Ser. No. 483,130, Apr. 8, 1983, abandoned.

[30] Foreign Application Priority Data

Apr. 26, 1982 [CH] Switzerland .................. 2514/82

[51] Int. Cl.$^5$ ............................................. C12P 7/06
[52] U.S. Cl. ................................... 435/161; 435/313; 435/314; 435/315
[58] Field of Search ................. 435/161, 313, 314, 315

[56] References Cited

U.S. PATENT DOCUMENTS

| | | | |
|---|---|---|---|
| 3,186,802 | 6/1965 | Gerrard | 422/234 X |
| 3,630,848 | 12/1971 | Lefrancois | 435/243 |
| 3,986,934 | 10/1976 | Müller | 435/812 X |
| 4,001,090 | 1/1977 | Kalina | 435/313 X |
| 4,207,180 | 6/1980 | Chang | 435/314 X |
| 4,329,433 | 5/1982 | Seebeck et al. | 435/255 |
| 4,346,113 | 8/1982 | Faust et al. | 435/161 X |
| 4,545,945 | 10/1985 | Präve et al. | 435/314 X |

FOREIGN PATENT DOCUMENTS

| | | | |
|---|---|---|---|
| 0022613 | 1/1981 | European Pat. Off. | 435/161 |
| 22613 | 1/1981 | European Pat. Off. | 435/161 |
| 603658 | 4/1978 | U.S.S.R. | 435/315 |
| 644821 | 1/1979 | U.S.S.R. | 435/315 |
| 2118967 | 11/1983 | United Kingdom . | |

Primary Examiner—Carolyn S. Elmore
Attorney, Agent, or Firm—Vogt & O'Donnell

[57] ABSTRACT

Alcohol is produced by continuous fermentation process in which must is fermented in a vat. Fresh must is introduced into the vat and fermented must is withdrawn from the vat. Fermented must withdrawn from the vat is pumped from the vat in a pumping column of a circuit extending above the vat in which carbon dioxide exerts mammoth pumping action. A back pressure is maintained and adjusted in an upper portion of the vat which is connected with the pumping column for concentrating carbon dioxide in the vat and for controlling the flow rate of the mammoth pumping column and the circulation speed of the must in the circuit. The pumping column is connected with a pipe which is connected to a lower portion of the vat which completes the circuit and which is disposed for effecting a turbulent flow of the carbon dioxide depleted must and for returning recycled must to the vat. Carbon dioxide is separated from the must in the pumping column and exerts the mammoth pumping action. A mixture of oxygen and inert gas is introduced into the turbulent flow of must in an upper portion of the return pipe.

13 Claims, 1 Drawing Sheet

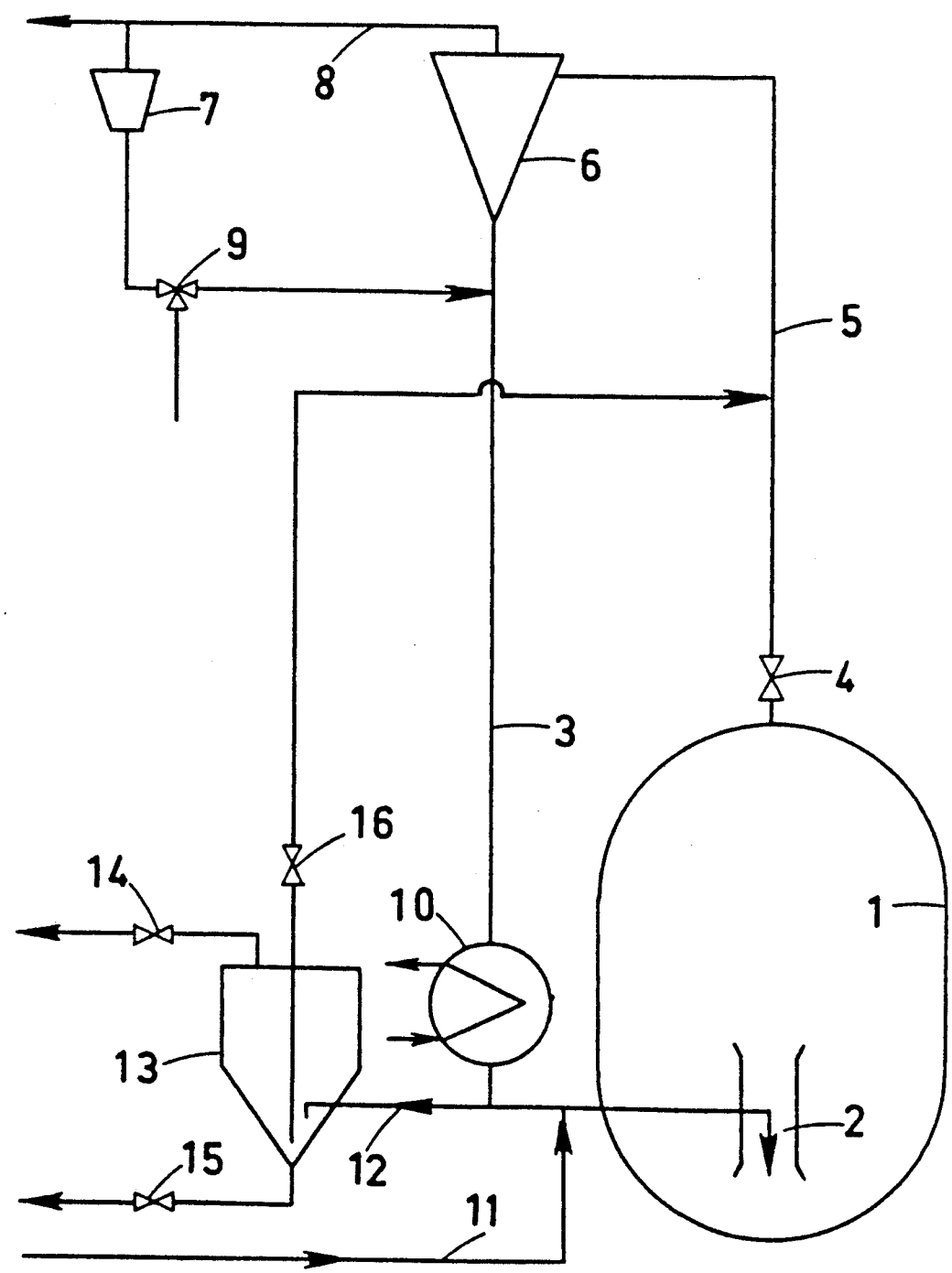

PROCESS FOR THE PRODUCTION OF ALCOHOL

CROSS REFERENCE TO RELATED APPLICATION

This is a continuation of co-pending application Ser. No. 06/774,184, filed Sept. 9, 1985, now abandoned which, in turn, is a continuation of application Ser. No. 483,130, filed on Apr. 8, 1983, now abandoned.

BACKGROUND OF THE INVENTION

This invention relates to a process for the production of alcohol (ethanol) by the continuous fermentation of a must being circulated in a closed circuit by a mammoth (air lift) pump, with fresh broth being continuously injected into the circuit and fermented broth being continuously removed from the circuit.

This invention also relates to a fermenter for the continuous production of alcohol, comprising a fermentation vat and a mammoth pump which are connected in a closed circuit, a device for injecting fresh broth and a device for removing fermented broth.

Several processes and fermenters for the continuous production of alcohol are known, in which the circulation of a culture medium rich in fermentable sugar and which is designated in the present specification by the term "must" is assured either by means of an ordinary pump, or by a mammoth pump fed via a compressor. A process is known in which the circulation is assured solely by the release of carbon dioxide gas produced during fermentation.

In this last-mentioned known process, the fermentation conditions vary considerably the further one moves up the fermentation vat, because of the expansion and the coalescence of ascending bubbles of carbon dioxide gas and, even if the yield in weight of alcohol obtained with respect to the weight of fermentable sugar used is good, the productivity is low compared to the size of the installation.

In the other processes mentioned above, it is possible to obtain suitable productivities as well as good yields which approach the theoretical maximum. The dilution rates, that is the ratio between the quantity of fresh must which is injected per hour and the quantity of must contained in the circuit, are fairly high, of the order of ten percent or multiples thereof. The active yeast content of the must is about 50 g of dry matter of yeast per liter, the fresh must which is injected contains from about 100 to 150 g of fermentable sugars per liter and the fermented must which is removed contains from about 6.5 to 8.5% of alcohol. All these quantities are substantial and are to be found in the best of these known processes and fermenters.

However, the dimensions of these fermenters and the quantities of must which are treated by these known processes are relatively modest, i.e., from a few liters to a few m³. The reason for this lies in the fact that it is very difficult to maintain homogeneous conditions favourable for alcoholic fermentation in a fermenter of several tens, even hundreds, of m³ without running into serious technical and economic difficulties. In effect, if good transfer to the yeast solely of the oxygen necessary for its anaerobic metabolism is to be supplied, it is necessary to assure on the one hand good agitation of the medium and, on the other hand, an adequate oxygen concentration in the gaseous phase. By increasing the dimensions of the fermenter, the inhomogeneity of the conditions prevailing in the fermentation medium are increased, notably as a function of the height of the vat. The restoration of this homogeneity would imply for the known fermenters and processes complicated devices for the injection of gas under a variable pressure and/or differential stirring devices distributed regularly over the complete height of the vat. The maintenance of this homogeneity could only be ensured by the expenditure of a very great stirring energy, at a prohibitive cost.

SUMMARY OF THE INVENTION

An object of the present invention is to provide a process and a fermenter for the continuous production of alcohol which may be realized on a large scale without running into the technical and economic difficulties which have been mentioned above.

To this end, the process according to the present invention is characterised in that the must in the lower part of a fermentation vat is stirred by the injection of a descending flow of recycled must, a back pressure is applied at the top of the vat so that the carbon dioxide gas which is released by the fermentation remains compressed in the upper part of the vat, the carbon dioxide gas is allowed to exert the mammoth pumping effect in a pumping column located above the vat, the must is recycled by being allowed to descend in a turbulent flow in a return pipe and a mixture of oxygen and inert gas is injected into the upper part of the return pipe.

Likewise, the fermenter according to the present invention is characterised in that the vat has in its lower part a hydraulic stirring device which is connected to a return pipe for the recycled must, a back pressure valve is provided at the top of the vat to prevent the expansion in the vat of the carbon dioxide gas which is released during fermentation, a mammoth pump is positioned above the back pressure valve to be actuated by means of said carbon dioxide gas in expansion, the return pipe connected to the top of the mammoth pump has in its upper part a device for injecting gas to supply the must with oxygen, and this return pipe is disposed so that it ensures a turbulent flow of the recycled must. The process and fermenter according to the present invention make it possible to achieve the object which has been set and they also have numerous advantages. In particular, their design is such that solely the quantity of oxygen necessary for the anaerobic action of the yeast need be injected into the must. Thus, it is possible to inject per hour a quantity of said gaseous mixture containing less than 0.15 ml of oxygen under atmospheric pressure per g of dry weight of yeast which is present in the must. These quantities are lower than those which are recommended in the known processes. It is by radically improving the conditions under which the oxygen is introduced into the must as well as the conditions prevailing in the vat that it is thus possible to dispense with any surplus oxygen and to avoid the risks of local triggering of aerobic fermentation and the risks of local inhibition of anaerobic fermentation.

Thus, the must can contain in solution in the fermentation vat the exact quantity of oxygen which is necessary for the anaerobic action of the yeast, and the agitation in the vat is sufficient for all of this oxygen to be effectively taken up by the yeast. In this manner, the agglutination phenomena of the yeast around the gas bubbles in the fermetation vat are avoided which would directly result in an overfeeding of oxygen to the agglutinated cells. Dilution of the oxygen in the gas bubbles is also avoided, for these would rise and expand while ascending in the fermentation vat, the adverse consequence of which would be a reduction in the transfer rate of the oxygen into the must.

The process and fermenter of the present invention are thus adapted to be realized on a large scale, in particular implying a quantity of must treated in the circuit of a volume of at least 50 m$^3$. The larger the vat, the more the realization of the favourable conditions is facilitated without necessitating any expenditure of energy for the stirring and circulation.

DESCRIPTION OF PREFERRED EMBODIMENTS

In order to carry out the present process, it is possible to use as the starting material a must preferably having a content of fermentable sugar of from 100 to 280 g/l, in addition to the nutrients which are required by yeast. The latter may be selected from among yeasts known for their suitability for the production of alcohol on the one hand and for the formation of aggregates which facilitate their sedimentation on the other hand.

Fresh must may be injected into the bottom of the circuit, for example, into the bottom of the return pipe, to obtain the most benefit from the stirring effect of the flow of recycled must on the vat. A quantity of fresh must corresponding to from 0.2 to 0.5 times the quantity of must present in the circuit is preferably injected per hour into the circuit, the must in the circuit being able to contain on average from 50 to 100 g in dry weight of yeast per liter.

It has been particularly noted above that it is possible to inject oxygen into the circuit in very moderate quantities which only cover the actual oxygen requirement of the yeast for its anaerobic action. In order to ensure a complete resorption of the oxygen in the must, steps may be taken for the residence time of the must in the return pipe to be long enough, and to provide a turbulence of the must in the upper part of the return pipe which is strong enough for the diameter of the bubbles of said gaseous mixture to remain fairly small. Thus, in a preferred embodiment of the present process, it is provided, on the one hand that the turbulence of the must in the upper part of the return pipe is strong enough for the diameter of the bubbles of said gaseous mixture injected into the must not to exceed about 4 mm at the time of their formation and, on the other hand for the residence time of the must in the return pipe to be at least 10 seconds.

The reason for the injection of a gaseous mixture instead of, for example, pure oxygen is that it is also possible to use an inert gas which is immediately resorbed in the must, leaving in the form of smaller bubbles the oxygen which it contained. Due to the fact that no more oxygen than necessary is injected, these residual bubbles remain separate and are resorbed for the most part before colliding and forming larger bubbles by coalescence which would not be resorbed before entering the fermentation vat.

Therefore, use is made of the double effect of the turbulence of the must which imposes a limit on the size of the injected bubbles, and of the dilution of the oxygen in an easily resorbable gas which makes it possible to rapidly reduce the diameter of the bubbles to a fraction of this limit size. A gaseous mixture which is very suitable may be produced with ambient air and with the carbon dioxide gas released during fermentation, and it preferably comprises one part by volume of air and at least five parts by volume of carbon dioxide gas.

Thus, the recycled must is charged with oxygen which is practically completely resorbed and, optionally, it entrains the fresh must when it enters at the bottom of the fermentation vat at a high speed due to the height of the return pipe. This kinetic energy may be effectively transmitted to the must which is located in the vat by an appropriate design of the shape of the bottom of the vat and the mouth of the return pipe.

The must may rise slowly, at a speed of about 1-2 cm/s for example, in the vat where it is possible to arbitrarily distinguish three successive zones, i.e., a stirring zone, a sedimentation zone and a $CO_2$ concentration zone. In the stirring zone, the fresh must is thus initially mixed with the recycled must and with the must which is in the bottom of the vat. In the sedimentation zone which represents the largest part of the vat, the yeast acts efficiently without being hindered by the stirring at the bottom of the vat or by the release of $CO_2$. The yeast may sediment faster than the must rises and thus it is possible to observe a concentrating effect on the yeast at the bottom of the sedimentation zone. Consequently, the recycled must contains less yeast per liter than the must in the fermentation vat, which facilitates the operation of a decanter which may be provided outside the fermentation vat, connected to the return pipe, for example, and which reduces the exposure of the yeast to oxygen during the passage of the yeast along the return pipe. In the $CO_2$ concentration zone, as in all of the fermentation vat, the release of $CO_2$ in the form of gas bubbles is hindered by the back pressure applied at the top of the vat, which guarantees homogeneous and optimal fermentation and sedimentation conditions for the yeast in the sedimentation zone.

Thus, it is only above the vat, in a pumping column, that the carbon dioxide gas is allowed to be released from the must, to form bubbles, to expand and to exert the mammoth pumping action. The circulation speed in this column may be very high, in the region of at least a few m/s, for example. At this speed, the foam which is formed is broken up and separation of the gases, in other words the degassing operation which has already been produced in part in the pumping column, may be completed in an efficient device such as a cyclone.

The design of the present process also makes it possible to realize a particular embodiment in which a pressure lower than atmospheric pressure is maintained at the top of the circuit in order to remove the alcohol from the fermented must by evaporation. Thus, it is possible to benefit from the advantages of an evaporative system, i.e., a higher yield and less inhibition due to the alcohol, without having the attendant disadvantages, i.e., the necessity of introducing large volumes of air under reduced pressure.

Once it has been degassed, the must runs out in a turbulent flow into the return pipe. In order to ensure this turbulent flow along the complete length of the return pipe, it should be possible to absorb pressure drops. This is one of the reasons why the process and the fermenter of the present invention are most advantageously produced on a large scale so that the necessary velocities, flow rates and heights may be obtained.

It is in this return pipe that the recycled must is preferably subjected to the cooling operation which is necessary to counterbalance the heating caused by the fermentation in the vat. Likewise, it is from this pipe, in particular from its lower part that, in one embodiment without an evaporative system, the fermented must charged with alcohol is preferably removed. The present process allows in this pipe a particularly efficient decanting due to the fact that the must has previously been degassed and that the small quantity of carbon dioxide gas which might then have been injected into the must cannot be desorbed due to the pressure exerted by the height of the return pipe. Thus it is possible to obtain decanting speeds of the yeast of about 20 cm/min. A decanting operation of this type makes it possible, on the one hand to remove must which is freed from the yeast and charged with alcohol and, on the other hand to remove from the circuit, if necessary, excess yeast. The decanted yeast which is not in excess may be recycled into the pumping column, for example solely under the effect of the pressure due to the height of the return pipe, without the aid of an auxiliary pump. The decanted must which is removed may have an alcohol content of, for example, from about 50 to 80 g/l.

The fermenter according to the present invention is characterised as indicated above. The hydraulic stirring device which is provided in the lower part of the vat is preferably of the Venturi type. To this end, the mouth of the return pipe may be located above the bottom of the vat, directed downwards and surrounded coaxially by a length of tube of a larger diameter than its own diameter and flaring at its two ends. The bottom of the vat may itself have a semi-spherical shape for example, which reinforces the action of the Venturi device. The center part of the vat may then have a cylindrical shape extending from the hemisphere of the bottom and may be capped by a hemisphere complementary to that of the bottom so that it is possible to channel the fermented must towards the back pressure valve.

This valve preferably has an adjustable flow rate so that it is possible to adjust, at will, and to control the flow rate of the mammoth pump and thus the circulation speed of the must in the circuit. The diameter and the height of the mammoth pump are selected as a function of the volume of the fermenter and of the flow rate of the must to be circulated. This flow rate is itself a function of the heat released by the reaction, and it should be fairly high so that the temperature gradient does not exceed a certain limit within the fermentation vat. This limit is in the region of a difference of about 3° C. between the top and the bottom of the vat.

Likewise, the dimensioning of the return pipe is effected as a function of the circulation speed of the must and in order to preferably observe the turbulence and residence time conditions described above. The turbulence may be influenced not only by the dimensioning of the pipe, but also by providing therein diaphragms or baffles, for example. Care should simply be taken that the fermenter is high enough to overcome the pressure drops related thereto which may exceed the equivalent of 2 m of water column.

The present fermenter may be provided at its top with a degassing device of, for example, the cyclone type. In effect, the circulation speed of the must in the fermenter upper part is such that it allows the use of this particularly efficient device.

The present fermenter preferably has a cooling device on a part, even on the largest part of its return pipe. This device may, for example, be in the form of a tubular heat exchanger in which the highly turbulent flow of must is reflected in a very high heat transfer coefficient.

Moreover, the present fermenter may advantageously be provided with an external decanter which is connected upstream to the bottom of the return pipe and downstream to the middle of the mammoth pump, for example. The decanter thus connected is capable of operating very efficiently without the aid of an auxiliary pump. On the one hand, its function is to provide fermented must which is charged with alcohol but freed from its yeast and, on the other hand, it is to recycle the decanted yeast, while allowing, if necessary, any excess yeast to be removed.

Finally, it is at the bottom of the return pipe that a pipe for supplying fresh must is preferably connected, so that this must may be directly entrained in the stirring device by the recycled must.

In a particular embodiment of the present fermenter, the top of the fermenter is connected, on the one hand, to a gas pumping device for producing a pressure lower than atmospheric pressure and, on the other hand, to a device for collecting alcohol vapours.

In this particular embodiment, it is also possible to provide a device for heating the top of the mammoth pump to provide for more effective release of the alcohol vapours. These vapours will be mixed with $CO_2$ which is released from the must and will have to be separated therefrom. Hence, the device for collecting the alcohol vapours preferably comprises a combination of condensation means and means for separating the alcohol and the $CO_2$.

BRIEF DESCRIPTION OF THE DRAWING

The fermenter according to the present invention is described in the following with reference to the accompanying drawing which schematically illustrates one preferred embodiment thereof.

DETAILED DESCRIPTION OF THE DRAWING

In this embodiment, a fermentation vat 1 has in its lower part a stirring device 2 of the Venturi type which is connected to a return pipe 3 for the recycled must. The vat has at its top an adjustable back pressure valve 4 to prevent the expansion in the vat of the carbon dioxide gas which is released during fermentation. A mammoth pump 5 is positioned above the back pressure valve 4 and is activated by means of the carbon dioxide gas delivered by said valve. The return pipe 3 is connected to the top of the mammoth pump 5 by means of a degassing device 6 of the cyclone type. A small compressor 7 is connected to a $CO_2$ removal pipe 8 for injecting into the top of the return pipe 3 a mixture of air and $CO_2$. Air is introduced into the gas injection device by a mixing valve 9. The return pipe 3 passes through a heat exchanger 10 for cooling the recycled must. A pipe 11 for the injection of fresh must is connected to the return pipe 3 just before it enters the vat 1. Likewise, a pipe 12 for removing must charged with alcohol and yeast is connected to the return pipe below the heat exchanger 10. This pipe 12 discharges into a pressurized decanter 13. A valve 14 for removing the fermented and decanted must makes it possible to adjust the quantity of must which is removed. A drainage valve 15 is provided for removing any possible excess of active yeast. Finally, a recycling valve 16 is provided for recycling, in the mammoth pump 5 under the effect of the pressure due to the height of the recycling pipe 3, a must charged with yeast recovered in the decanter 13.

EXAMPLES

The fermentation process according to the present invention is illustrated in the following by two Examples, in which the yeast which is used is (*Saccharomyces*

*cerevisiae*) CBS 2961 yeast, the flocculation qualities of which may be considered as relatively good.

EXAMPLE 1

An embodiment of the process according to the present invention is implemented in a fermenter corresponding to the embodiment illustrated in the drawing. The fermenter has a total volume of 300 m$^3$ and a total height of 23.5 m. The fermentation vat has a hemispherical bottom and a hemispherical top, a height of 8.5 m and a diameter of about 7.5 m. The average diameters of the mammoth pump and of the return pipe are respectively about 75 and 60 cm.

60 m$^3$/h of fresh must containing 150 g/l of fermentable sugar are injected into the bottom of the return pipe. 6 m$^3$ of air per h mixed with 60 m$^3$ per h of $CO_2$ recovered at the outlet of the degassing cyclone are injected into the top of the return pipe. The content of active yeast in the must in the fermenter is 65 g of dry matter per l.

The flow rate through the back pressure valve on the vat is adjusted so that the average circulation speed of the must is about 2 m/s in the mammoth pump, about 6 m/s in the degassing cyclone and about 1.5 m/s in the return pipe. The average residence time of the must in the vat is 10 min. The residence time of the must in the return pipe is on average 15 seconds. The turbulence in the return pipe is such that the bubbles of the injected gas mixture have a diameter which hardly exceeds 3.5 mm in the upper part of the pipe.

60 m$^3$ per h of must having an alcohol content of 8.5% by volume are removed from the fermenter.

EXAMPLE 2

An embodiment of the process according to the present invention is implemented in a fermenter similar to the one which is schematically illustrated in the drawing, but which also has at its top a device for pumping the alcohol vapours. The fermenter is higher by 10 m than the one of Example 1.

135 m$^3$ per h of fresh must containing 265 g/l of fermentable sugar are injected into the bottom of the return pipe. 9 m$^3$ of air per h mixed with 90 m$^3$ per h of $CO_2$ recovered at the outlet of the pumping device are injected into the top of the return pipe. The content of active yeast in the must in the fermenter is 50 g of dry matter per l.

A pressure of 70 mbar is applied to the top of the fermenter and the upper part of the mammoth pump is heated to a temperature of 36° C. The alcohol vapours are separated from the $CO_2$ by any suitable device comprising a condensation trap and a water separator. 90% of the alcohol are recovered by this means and the remaining 10% are recovered by the decanter. A total productivity of 120 g of alcohol per l of fresh injected must is obtained.

We claim:

1. A continuous fermentation process for the production of alcohol comprising:
   introducing must into a bottom of a fermentation vat;
   fermenting the must in the vat with a yeast, which is suitable for the production of alcohol and which aggregates and sediments during the fermentation;
   maintaining a back pressure in the vat during the fermentation, by means of a back pressure valve positioned in a top of the vat, for compressing and inhibiting expansion of carbon dioxide evolved from fermenting must in the vat for hindering formation of carbon dioxide gas bubbles in the fermenting must;
   transferring fermented must and evolved carbon dioxide from the vat through the back pressure valve to a pumping column extending above the top of the vat for allowing the carbon dioxide released into the pumping column to expand in the column for exerting a mammoth pumping action on the fermented must for pumping the fermented must in the column;
   separating carbon dioxide from the pumped must in a degassing device connected with the pumping column above the vat for depleting carbon dioxide from the pumped must;
   conveying the carbon dioxide depleted must from the degassing device in a pipe, which is connected to the bottom of the vat, in a turbulent flow;
   introducing a mixture of oxygen and carbon dioxide into the turbulent flow of carbon dioxide depleted must in an upper portion of the pipe, the oxygen being introduced in an amount sufficient for obtaining only an amount of oxygen in the fermenting must in the vat which is necessary for maintaining the fermentation action of the yeast in the vat for producing alcohol;
   conveying gasified must in the pipe into the bottom of the vat in a turbulent flow for recycling must;
   controlling the flow rate of the fermented must, the carbon dioxide depleted must and the gasified must by means of the back pressure valve; and
   collecting alcohol from the fermented must.

2. A process according to claim 1 wherein the carbon dioxide introduced into the carbon dioxide depleted must comprises carbon dioxide separated from the fermented must.

3. A process according to claim 1 wherein the mixture of oxygen and carbon dioxide introduced into the carbon dioxide depleted must comprises one part by volume of air and at least five parts by volume of carbon dioxide.

4. A process according to claim 1 or 3 wherein the turbulence of the must in the pipe is sufficient for obtaining bubbles of the mixture of oxygen and carbon dioxide in the gasified must having a size not exceeding 4 mm.

5. A process according to claim 4 wherein the residence time of the gasified must in the pipe is at least 10 seconds.

6. A process according to claim 1 wherein gasified must is collected from the pipe and decanted for collecting alcohol from the collected gasified must.

7. A process according to claim 6 further comprising cooling the gasified must in the pipe for collecting cooled gasified must in the decanter for collecting alcohol from the cooled collected gasified must.

8. A process according to claim 6 further comprising recycling decanted yeast to the pumping column.

9. A process according to claim 1 further comprising producing a pressure less than atmospheric pressure in a top portion of the pumping column for collecting alcohol from the pumped must.

10. A process according to claim 9 further comprising heating the pumped must for assisting in collecting the alcohol from the must.

11. A process according to claim 1 wherein the gasified must introduced into the vat by the pipe drives a hydraulic stirring device for stirring the must fermenting within the vat.

12. A process according to claim 1 further comprising introducing fresh must into the gasified must in the pipe for introducing fresh must into the vat.

13. A process according to claim 1 wherein the fresh must is introduced into the gasified must in a quantity of from 0.2 times to 0.5 times the quantity of must in the pumping column and pipe.

* * * * *